United States Patent [19]

Verheyden et al.

[11] Patent Number: 4,565,868

[45] Date of Patent: Jan. 21, 1986

[54] PROCESS FOR PREPARING GUANINE DERIVATIVES

[75] Inventors: Julien P. H. Verheyden, Los Altos; John C. Martin, Redwood City, both of Calif.

[73] Assignee: Syntex (U.S.A.) Inc., Palo Alto, Calif.

[21] Appl. No.: 537,237

[22] Filed: Sep. 29, 1983

Related U.S. Application Data

[63] Continuation-in-part of Ser. No. 464,274, Feb. 7, 1983, which is a continuation-in-part of Ser. No. 431,933, Sep. 30, 1982.

[51] Int. Cl.⁴ .................... C07D 473/18; A61K 31/52

[52] U.S. Cl. .................... 544/276; 544/277; 514/262

[58] Field of Search ................ 544/277, 276; 424/253

[56] References Cited

U.S. PATENT DOCUMENTS 4,347,360 8/1982 Ogilire .................... 544/276
4,461,757 7/1984 Ogilire .................... 544/277

Primary Examiner—Nicholas S. Rizzo
Attorney, Agent, or Firm—Annette M. Moore; Tom M. Moran

[57] ABSTRACT

1-Monophosphate esters, 1,3-bisphosphate esters and cyclic phosphate esters of 9-(1,3-dihydroxy-2-propoxymethyl)guanine are useful as antiviral agents.

18 Claims, No Drawings

PROCESS FOR PREPARING GUANINE DERIVATIVES

This is a continuation-in-part of U.S. Ser. No. 464,274 filed Feb. 7, 1983, which is a continuation-in-part of U.S. Ser. No. 431,933 filed Sept. 30, 1982.

BACKGROUND OF THE INVENTION

1. Field of the Invention

This invention relates to phosphate and cyclic phosphate esters of 9-(1,3-dihydroxy-2-propoxymethyl)guanine and compositions containing the same which are useful in treating viral infections in warm blooded and cold blooded animals. This invention also relates to a process for preparing these compounds.

2. Related Disclosure

Viral infections are widespread and result in a wide variety of symptoms. Some viral infections are easily overcome by the body's defense mechanism while others are of a more serious nature leading to permanent damage, e.g., blindness, and even to death. One such family of viruses which may cause serious infections is the Herpes virus group.

The drugs presently used to treat viral infections are ineffective in many cases or, if effective, are needed in large and/or continuous dosages which produce serious side-effects and/or toxicity. Therefore there is a need for an effective antiviral agent which is effective at lower dosages than the presently available drugs, thus diminishing the chance of possible side-effects and toxicity.

U.S. Pat. No. 4,199,574 discloses compounds represented by the following generic formula:

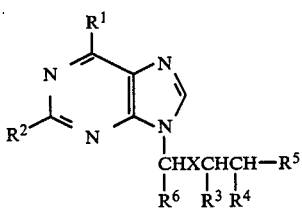

wherein X is sulphur or oxygen, $R^1$ is hydrogen, halogen, hydroxy, alkoxy, azide, thio, alkylthio, amino, alkylamino or dialkylamino; $R^2$ is hydrogen, halogen, alkylthio, acylamino, amino or azide; $R^3$ is hydrogen, straight or branch chain or cyclic alkyl, hydroxyalkyl, benzyloxyalkyl or phenyl; $R^4$ is hydrogen, hydroxy or alkyl; $R^5$ is hydrogen, hydroxy, amino, alkyl, hydroxyalkyl, benzyloxy, benzoyloxy, benzoyloxymethyl, sulphamoyloxy, phosphate, carboxypropiamyloxy, straight chain or cyclic acyloxy having from 1 to 8 carbon atoms e.g., acetoxy or substituted carbamoyl group of formula NHCO—Z wherein Z is alkyl, aryl or aralkyl optionally substituted by one or more of sulphonyl, amino, carbamoyl or halogen; $R^6$ is hydrogen or alkyl, provided that when X is oxygen and $R^2$, $R^3$, $R^4$, and $R^6$ are hydrogen, $R^1$ is not amino or methylamino when $R^5$ is hydrogen or hydroxy, or a salt thereof.

The class of compounds represented by the above formula and the pharmaceutically acceptable acid addition salts thereof are described to exhibit antiviral activity. See also *Tetrahedron Letters*, 21, 327-30 (1980), U.S. 4,323,573 and European application No. 49,072.

SUMMARY OF THE INVENTION

It has now been discovered that phosphate and cyclic phosphate esters of 9-(1,3-dihydroxy-2-propoxymethyl)guanine and the salts thereof are particularly active antiviral agents.

The present invention relates to compounds of the following formula

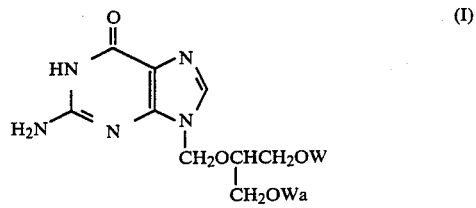

wherein W is hydrogen or

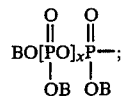

Wa is

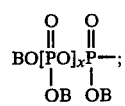

or W together with Wa is

wherein each B is independently hydrogen or a pharmaceutically acceptable counterion and x is 0, 1 or 2.

Another aspect of the invention is compositions containing the compounds of formula (I).

A further aspect of the invention is a method of treating viral infections in warm blooded and cold blooded animals using the compounds of formula (I) or a composition containing same as an active ingredient.

Yet another aspect of the invention is a process for preparing compounds of formula (I).

DETAILED DESCRIPTION AND PREFERRED EMBODIMENT

Broadly, the present invention relates to compounds of the following formula

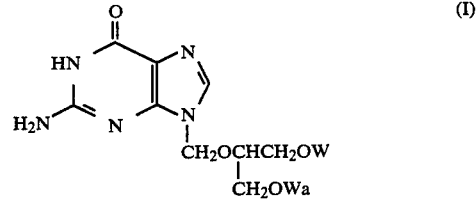

wherein W is hydrogen or

Wa is

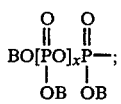

or W together with Wa is

wherein each B is independently hydrogen or a pharmaceutically acceptable counterion and x is 0, 1 or 2.

A preferred group of compounds of formula (I) is that wherein W is hydrogen and Wa is

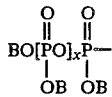

Within this group it is preferred that x is 0. Particularly preferred are compounds wherein at least one B is a pharmaceutically acceptable counterion especially the sodium ion, the potassium ion, the ammonium ion or the morpholinium ion.

As used in the specification and appended claims, unless specified to the contrary, the following terms have the meaning indicated.

"Pharmaceutically acceptable counterions" refers to both inorganic and organic counterions. Inorganic counterions include ammonium, the ions of sodium, potassium, lithium, calcium, magnesium, and the like. Particularly preferred are the potassium ion, the sodium ion and ammonium. Counterions derived from organic non-toxic bases include counterions of primary, secondary, and tertiary amines, substituted amines including naturally occurring substituted amines and cyclic amines such as isopropylamine, trimethylamine, diethylamine, triethylamine, tripropylamine, ethanolamine, 2-dimethylaminoethanol, morpholine 2-diethylaminoethanol, tromethamine, dicyclohexylamine, ethylenediamine, glucosamine, N-methylglucamine, piperazine, piperidine, N-ethylpiperidine, and the like. Preferred organic non-toxic counterions are those derived from N-methylglucamine, diethylamine, piperazine, morpholine, and dicyclohexylamine. Other useful amines are those disclosed in J. Pharm Sci, 66, 1(1977) incorporated herein by reference.

As used herein the following group when bonded to the oxygen of compounds of formula (I)

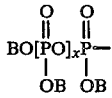

is referred to as a "monophosphate ester" when x is 0, as a "diphosphate ester" when x is 1 and as a "triphosphate ester" when x is 2. When only one of W or Wa is a phosphate ester, the compound of formula (I) is referred to as a (mono, di or triphosphate ester) and when both W and Wa are phosphate esters the compound of formula (I) is referred to as a bis(mono, di or triphosphate ester). For example, the compound of formula (I) wherein W is hydrogen and Wa is the above phosphate group wherein B is hydrogen and x is 0 is named as 1-(monophosphate ester) of 9-(1,3-dihydroxy-2-propoxymethyl)guanine. When W and Wa are both the above phosphate group wherein B is hydrogen and x is 1 the compound of formula (I) is named as 1,3-bis(diphosphate ester) of 9-(1,3-dihydroxy-2-propoxymethyl)guanine. The group

when bonded to the oxygens of compounds of formula (I) is referred to as a "cyclic pnosphate ester".

It is understood that when compounds of the instant invention can exist as optical isomers, both the isomers and the racemic mixture are encompassed within the invention.

UTILITY AND ADMINISTRATION

The subject compounds of formula (I) exhibit potent antiviral activity when administered to warm blooded and cold blooded animals, particularly mammals, birds, and fish, but most particularly humans. For example, the compounds of the present invention exhibit excellent activity against Herpes Simplex virus I and II and related viruses such as cytomegalovirus, Epstein-Barr virus and varicella Zoster virus as well as viral hepatitis such as hepatitis B.

Pharmaceutical compositions, both veterinary and human, containing the subject compound appropriate for antiviral use are prepared by methods and contain excipients which are well known in the art. A generally recognized compendium of such methods and ingredients is Remington's Pharmaceutical Sciences by E. W. Martin, (Mark Publ. Co., 15th Ed., 1975). Liposomes may also be employed as pharmaceutical compositions for the compounds of formula (I), using methods known to those in the art [for example, as described in Szoka, F. Jr. et al, Ann.Rev.Biophys.Bioeng. 9:467–508 (1980), Schullery, S. E. et al, Biochemistry 19: 3919–3923 (1980) and Gregoriadis, G. et al, "Liposomes in Biological Systems," John Wiley and Sons (1980)].

The compounds of the invention may be administered parenterally (for example, by intraveneous, subcutaneous, intraperitoneal or intramuscular injection), orally, topically, intranasally or rectally.

The compositions are administered orally or parenterally at dose levels of about 0.1 to 300 mg/kg of compound of formula (I), preferably 1.0 to 60 mg/kg of mammal body weight, and are used in man in a unit dosage form, administered one to five times daily in the amount of 10 to 1000 mg per unit dose. For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated. The amount of compound of formula (I) in the formulation may vary from 0.1 percent weight (% w) to 99% w or more of the compound based on the total formulation and about 1% w to 99.9% w excipient. Preferably tne compound is present at a level of 10%–95% w.

For parenteral administration or for administration as drops, as for eye infections, the compounds may be presented in aqueous solution in a concentration of from about 0.1 to 10%, more preferably about 0.1 to 7%. The solution may contain antioxidants, buffers, and other suitable additives.

Alternatively for infections of the eye, or other external tissues, e.g. mouth and skin, the compositions are preferably applied to the infected part of the body of the patient topically as an ointment, cream, aerosol or powder, preferably an an ointment or cream. The compounds may be presented in an ointment, for instance with a water soluble ointment base, or in a cream, for instance with an oil in water cream base, in a concentration of from about 0.01 to 10%; preferably 0.1 to 7%, most preferably about 4.0% w/v. Additionally, viral infections may be treated by use of a sustained release drug delivery system as is described in U.S. Pat. No. 4,217,898.

For aerosol administration, the active ingredient is preferably supplied in finely divided form along with a surfactant and a propellant. Typical percentages of active ingredients are 0.01 to 20% by weight, preferably 0.04 to 1.0%.

Surfactants must, of course, be non-toxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olestearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the trademark "Spans") and the polyoxyethylene and polyoxypropylene derivatives of these esters. Mixed esters, such as mixed or natural glycerides may be employed. The preferred surface-active agents are the oleates or sorbitan, e.g., those sold under the trademarks "Arlacel C" (Sorbitan sesquioleate), "Span 80" (sorbitan monooleate) and "Span 85" (sorbitan trioleate). The surfactant may constitute 0.1–20% by weight of the composition, preferably 0.25–5%.

The balance of the composition is ordinarily propellant. Liquefied propellants are typically gases at ambient conditions, and are condensed under pressure. Among suitable liquefied propellants are the lower alkanes containing up to five carbons, such as butane and propane; and preferably fluorinated or fluorochlorinated alkanes, such as are sold under the trademark "Freon." Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

The compounds of the present invention or compositions containing same are also useful in treating non-human mammals, birds, e.g., chickens and turkeys, and cold-blooded animals, e.g., fish. For example, the compounds of the present invention and compositions containing same exhibit antiviral activity against the following non-human viruses:
Sciruid herpesvirus 1
Cavlid herpesvirus 1
Lagomorph herpesvirus 1
Phasianid herpesvirus 1
Phasianid herpesvirus 2 (Marek's disease)
Turkey herpesvirus 1
Anatid herpesvirus 1
Catfish herpesvirus 1
Equid herpesvirus 3
Bovid herpesvirus 1
Bovid herpesvirus 2
Bovid herpesvirus 3
Bovid herpesvirus 4
Pig herpesvirus 1
Pig herpesvirus 2
Murid herpesvirus 1
Cebid herpesvirus 1
Cebid herpesvirus 2
Tupaiid herpesvirus 1
Canine herpesvirus 1
Feline herpesvirus 1
Equid herpesvirus 1
Equid herpesvirus 2

Avian viral diseases such as Marek's disease and the like are prevented and/or treated by compounds of the present invention by methods well-known in the veterinary art such as by injecting the birds with the composition containing the compound, or by adding the compound of the instant invention to feed or drinking water.

Fish which are in a confined area such as a pool, uarium or holding tank may also be treated for viral infections such as herpeslike viruses, e.g., channel catfish virus (CCV), herpes-virus salomones, Nerka virus and the like by adding the compound directly to the water of the pool, aquarium or holding tank or by incorporating the compounds into the feed.

The exact regimen for administration of the compounds and compositions disclosed herein will necessarily be dependent upon the needs of the individual subject being treated, the type of treatment and, of course, the judgement of the attending practitioner.

Preparation

The compounds of formula (I) may be prepared from compound of formula (X) which is prepared by Reaction Sequence (II). Compound of formula (V) which is an intermediate used in Reaction Sequence (II) is prepared by Reaction Sequence (I).

REACTION SEQUENCE (I)

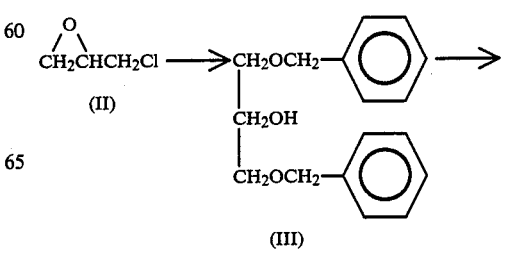

-continued
REACTION SEQUENCE (I)

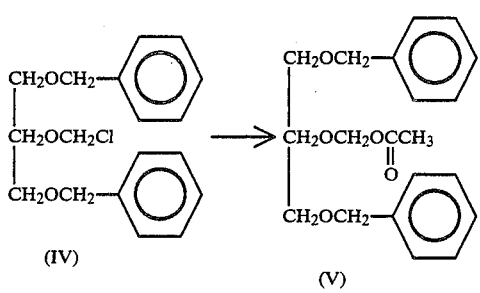

REACTION SEQUENCE (II)

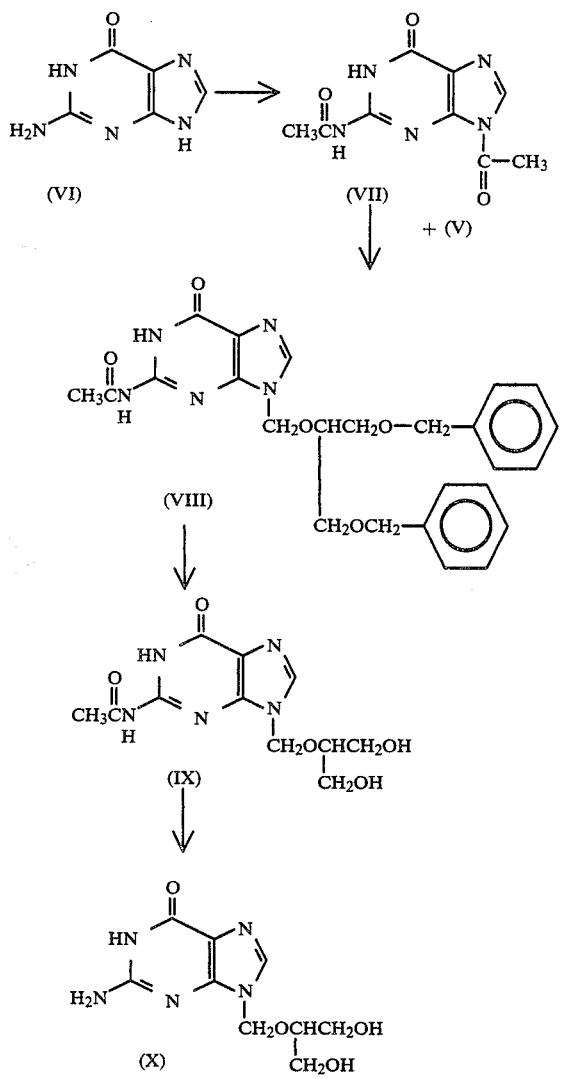

In Reaction Sequence (I) the compound of formula (III) is prepared by adding epichlorohydrin (II) dropwise to a solution of an alkali metal salt, preferably the sodium salt, of optionally substituted benzyl alcohol in a solvent such as dimethylformamide, dimethylacetamide, hexamethylphosphoramide, dimethylsulfoxide, sulfolane, tetrahydrofuran, and dioxane at a temperature of about 0° C. to 100° C., preferably at about 15° C. to 40° C. The reaction mixture is stirred from about 10 hours to 24 hours, preferably from about 12 hours to 18 hours at a temperature of about 0° C. to 100° C., preferably from about 20° C. to 50° C.

Compound of formula (III) is chloromethylated to compound of formula (IV) by bubbling dry hydrogen chloride gas in a solution of the compound and paraformaldehyde dissolved in a halogenated hydrocarbon solvent such as dichloroethane, chloroform, dichloromethane, and 1,1,2-trichloroethane cooled to a temperature of about 0° C. to 25° C., preferably at a temperature of about 0° C. The hydrogen chloride gas is added over 30 minutes to 3 hours, preferably over 1 hour to 2 hours until the paraformaldehyde dissolves. The solution is held at a temperature from about 0° C. to 10° C. for about 12 hours to 48 hours, preferably from about 0° C. to 5° C. for about 16 hours to 24 hours.

Compound of formula (V) is prepared by reacting an alkali metal acetate such as sodium acetate with compound of formula (IV) dissolved in a solvent such as dimethylformamide, tetrahydrofuran, dimethylacetamide, hexamethylphosphoramide, dimethylsulfoxide, sulfolane, and dioxane at a temperature of about 0° C. to 45° C., preferably from about 0° C. to 25° C. The solution is stirred from about 5 to about 24 hours, preferably from about 10 hours to about 18 hours at a temperature of about 10° C. to about 30° C., preferably at a temperature of about 15° C. to 25° C.

In Reaction Sequence (II) compound of formula (VII) is prepared by heating guanine (VI) with acetic anhydride, neat, at reflux for about 10 to 24 hours, preferably for about 12 to 18 hours.

$N^2$, 9-Diacetylguanine of formula (VII) is reacted with compound of formula (V) to form compound of formula (VIII) neat or in a solvent such as dioxane, sulfolane and the like in the presence of a catalytic amount of an acid such as bis(p-nitrophenyl)phosphate, toluene sulfonic acid, methylphosphonic acid or dichloroacetic acid, preferably bis(p-nitrophenyl)phosphate at a temperature of about 75° C. to 200° C., preferably at about 110° C. to 180° C. The reaction is generally carried out using 0.8 moles to 1.2 moles of compound of formula (V) to one mole of compound of formula (VII).

The benzyl protecting groups are removed from compound of formula (VIII) by catalytic hydrogenation to form compound of formula (IX). A catalyst such as palladium on carbon in a slurry is added to a solution of compound of formula (VIII) dissolved in a solvent such as aqueous methanol. Hydrogen is added to the solution at a pressure of 15 psi to 200 psi, preferably at a pressure of 30 psi to 80 psi.

Compound of formula (X) is prepared by deacetylating compound of formula (IX) with a base such as ammonia dissolved in an alcohol such as methanol. A solution of compound of formula (IX) and the base is stirred for about 5 hours to 36 hours, preferably for about 10 hours to 24 hours at a temperature of about 10° C. to 30° C., preferably at a temperature of about 15° C. to 25° C.

Compounds of formula (I) wherein W is hydrogen and Wa is —P(O)(OH)$_2$ may be prepared by Reaction Sequence (III).

REACTION SEQUENCE (III)

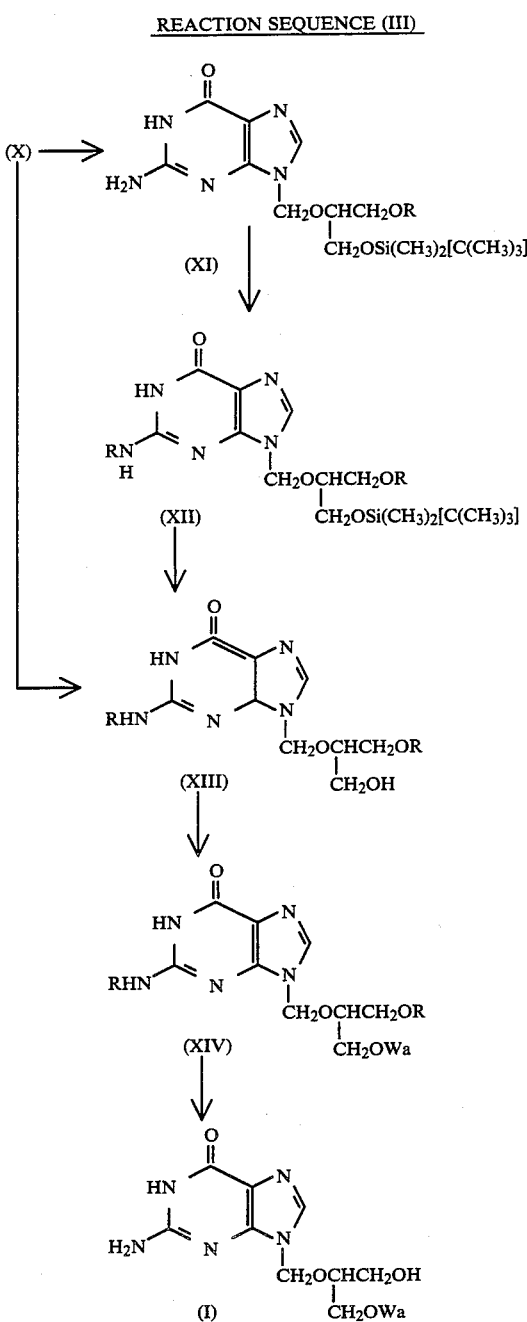

wherein R is benzoyl or a triphenylmethyl group.

In Reaction Sequence (III) compound of formula (X) is reacted with a silyl protecting compound such as t-butyldimethylsilyl chloride in a solvent such as dimethylformamide, N-methylpyrrolidone, pyridine, and the like. The reaction mixture is stirred at a temperature of −5° C. to room temperature, preferably at 0° C. for 1/2 to 4 hours, preferably for 2 hours. The resultant syrupy residue is added to water whereupon compound of formula (XI) precipitates. Compound of formula (XI) dissolved in a solvent such as pyridine, lutidine, dichlorometnane containing triethylamine, and the like is reacted with benzoyl chloride at a temperature of −5° C. to 10° C., preferably at 0° C. The mixture is allowed to warm to room temperature. After 18 to 36 hours, preferably 24 hours, the solvent is evaporated and crude compound of formula (XII) is partially purified by conventional means such as chromatography. Compound of formula (XIII) is prepared by treating compound of formula (XII) with an acid such as 80% acetic acid at 50° C. to 100° C., preferably 80° C. for 1 to 6 hours preferably 3 to 4 hours which removes the silyl protecting group.

Compound of formula (XIV) is prepared from compound of formula (XIII) by treatment with a phosphorylating agent such as pyrophosphoryl chloride. Compound of formula (XIII) in a solvent such as ethyl acetate, acetonitrile, cresol and the like, preferably ethyl acetate, is cooled to −5° C. to 10° C., preferably 0° C. The phosphorylating agent such as pyrophosphoryl chloride is added. The reaction is quenched by the addition of ice after 1 to 4 hours, preferably after 1½ to 3 hours. The reaction mixture is neutralized by addition of a base such as sodium hydrogen carbonate. Compound of formula (XIV) is recovered and hydrolyzed with a base such as ammonium hydroxide, sodium hydroxide and the like to produce compound of formula (I). Compound of formula (I) wherein W is hydrogen and Wa is —P(O)(OH)$_2$ is recovered as its salt by means well known in the art such as chromatography.

Another method for preparing compound of formula (I) comprises reacting a compound of formula (X) with a triphenylmethyl protecting agent such as triphenylmethyl chloride (trityl chloride), 4-methoxyphenyl(diphenyl)methyl chloride and the like to form compound of formula (XIII) wherein R is a triphenylmethyl group. A solution of compound of formula (X), the protecting agent and a catalytic amount of an amine such as 4-dimethylaminopyridine or triethylamine in a solvent such as dimethylformamide, pyridine, and the like is reacted for ½ to 4 hours, preferably for 1 to 3 hours at 25° C. to 60° C., preferably for 30° C. to 50° C. Compound of formula (XIII) is purified by silica gel column chromatography.

Compound of formula (XIV) wherein R is a triphenylmethyl group is prepared by reacting a compound of formula (XIII) wherein R is a triphenylmethyl group with a phosphorylating agent such as cyanoethylphosphate. The reactants, in a solvent such as pyridine, lutidine and the like are reacted in the presence of a condensing agent such as dicyclohexylcarbodiimide at 15° C. to 30° C., preferably from 20° C. to 30° C. for 1 to 5 days, preferably for 1½ to 3 days, followed by evaporation and treatment of the residue with ammonium hydroxide for from 1 to 12 hours, preferably 1½ to 8 hours, at about 40° C. to 90° C., preferably 50° C. to 80° C. Compound of formula (XIV) wherein R is a triphenylmethyl group is converted to the monoammonium salt of compound of formula (I) by removing the protecting groups with an acid such as acetic acid followed by a base such as ammonium hydroxide. Compound of formula (I) is recovered by gel chromatography.

Compound of formula (XIV) wherein R is a triphenylmethyl group can also be prepared by reacting a compound of formula (XIII) wherein R is a triphenylmethyl group with a phosphorylating agent such as bis (p-nitrophenylethyl)phosphorochloridate [prepared according to the method described in Tet. Lett. 23, 4793 (1982)] in a solvent such as pyridine, lutidine and the like at about room temperature for about ½ hour to 3 days, preferably 18 hours to 36 hours. Tne product of this reaction is reacted with 1,5-diazabicyclo[5.4.0]undecene-5 in a solvent such as pyridine at about room temperature for about ½ hour to 3 days, preferably 18 hours to 36 hours. Compound of formula (XIV) wherein R is a triphenylmethyl group, recovered by chromatography, is converted to the monoammonium salt of compound of formula (I) by removing the protecting groups with an acid such as acetic acid followed by a base such as ammonium hydroxide.

Compounds of formula (I) wherein W and Wa are $-P(O)(O^-Na^+)_2$ may be prepared by the following Reaction Sequence.

REACTION SEQUENCE IV

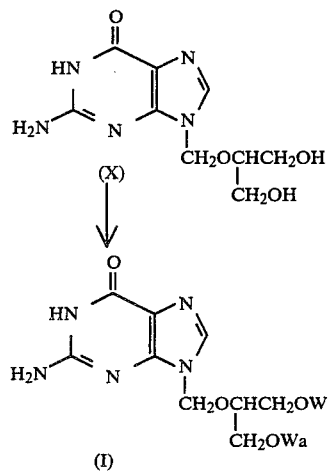

wherein W and Wa are as defined above.

In Reaction Sequence (IV) compound of formula (1) wherein W and Wa are as defined above may be prepared by reacting compound of formula (X) with a phosphorylating agent such as pyrophosphoryl chloride. Compound of formula (X) in a solvent such as ethyl acetate, acetonitrile, dioxane and the like, preferably ethyl acetate, is cooled to $-5°$ C. to 10° C., preferably to 0° C. The phosphorylating agent is added dropwise over 2 to 5 minutes, preferably over 3 minutes. After 1 to 4 hours, preferably after 2 hours, the reaction is quenched by adding ice followed by neutralizing with a base such as sodium hydrogen carbonate. Compound of formula (I) is recovered by conventional means such as chromatography followed by recrystallization.

Compounds of formula (I) wherein W together with Wa is a cyclic phosphate ester are prepared by cyclizing compounds of formula (I) wherein W is hydrogen and Wa is $P(O)(O^-Na^+)_2$. This compound is converted to the free acid by passing a solution containing the compound through an ion exchange resin such as Dowex 50-X8 ($H^+$ form) available from Dow Chemical Co. The free acid is converted to a salt of the formula:

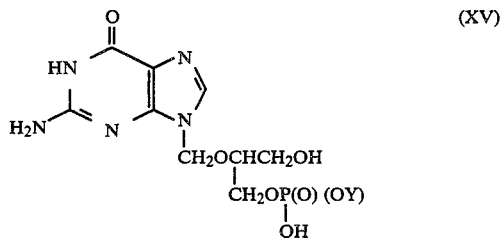

wherein Y is a lipophilic amine by treatment with a lipophilic amine such as 4-morpholino-N,N'-dicyclohexylcarboxamidine prepared according to the method described in *J. Am. Chem Soc.*, 83:649 (1961) in a solvent mixture such as pyridine/water. The resultant intermediate in a solvent such as pyridine, lutidine, and the like is added dropwise to a refluxing solution of a condensing agent such as dicyclohexylcarbodiimide, available from, i.a., Aldrich Chemical Co., in a solvent such as pyridine, lutidine, and the like. When addition is complete the mixture is refluxed for 1½ to 4 hours, preferably for 2 to 3 hours. The cyclic phosphate ester is recovered as the salt such as the potassium or trialkylammonium salt after preparative high pressure liquid chromatography by eluting with, e.g., a potassium phosphate buffer or a trialkylammonium carbonate solution.

To prepare the compounds of formula (I) wherein x is 1 the morpholinophosphate derivative of compounds of formula (I) (X=0) are prepared by reacting compound of formula (X) or compound of formula (XIII) with morpholino-dibenzotriazole phosphate as described in Nucl. Ac. Res. 10, 2337 (1982). The benzotriazole ring is removed by the method discussed on p. 2347 of the above article to form a compound of the formula

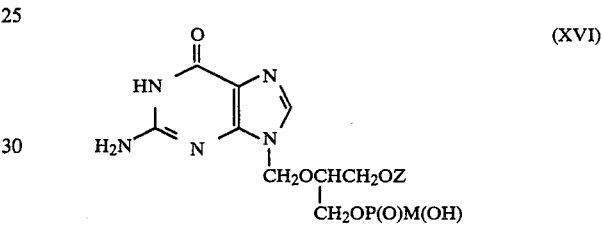

wherein M is 4-morpholino and Z is hydrogen or $P(O)M(OH)$. This compound is reacted with 0.5M tributylammonium phosphate in dimethylformamide at 50° C. for 16 hours as described in J. Org. Chem., 46, 2246 (1981) to form compounds of formula (I) wherein x is 1, for example, 1-mono(diphosphate ester) of 9-(1,3-dihydroxy-2-propoxymethyl)guanine. The triphosphate of compounds of formula (I) (compounds wherein x is 2), for example, 1,3-bis(triphosphate ester) of 9-(1,3-dihydroxy-2-propoxymethyl)guanine, are prepared by reacting the above morpholinophosphate compound with 0.5M tributylammonium pyrophosphate in dimethylformamide at 40° C. for 6 hours. The triphosphate of compounds of formula (I) may also be prepared from the monophosphate by the methods disclosed in J. Am. Chem. Soc., 87, 1785 (1965) and Nuc. Ac. Res., 9, 2003 (1981).

Compounds of formula (I) wherein B is hydrogen, i.e., the free acid, may be prepared by passing a solution of a compound of formula (I) wherein B is a counterion such as an alkali metal ion, e.g. the sodium or potassium ion through an ion exchange resin as is described above.

Compounds of formula (I) wherein B is a counterion, particularly the alkali metal ions or ammonium ion may be prepared in situ as illustrated in Reaction Sequence III and (IV) or by ion exchange of the calcium ion with the desired counterion. The calcium salt is prepared by mixing an alcoholic, e.g., ethanolic, solution of calcium chloride with a compound of formula (I) wherein B is a counterion such as the sodium or potassium ion dissolved in an alcohol such as ethanol. The resulting calcium salt precipitates out. The calcium salt is transformed into other desired salts by ion exchange by passing a solution containing the calcium salt through an appropriate cation exchange resin such as a Dowex 50 resin available from Dow Chemical Co. containing the desired counterion.

Alternatively, compounds of formula (I) wherein B is a pharmaceutically acceptable counterion may be prepared by first forming the free acid as is described above and then reacting the free acid with the appropriate counterion source.

The following specific description is given to enable those skilled in the art to more clearly understand and practice the invention. It should not be considered as a limitation upon the scope of the invention but merely as being illustrative and representative thereof.

PREPARATION I

Preparation of 1,3-Di-O-benzylglycerol

Sodium hydride (100 g (50% dispersion in mineral oil), 2.08 mol) was washed twice with 1 l of hexane then dried under nitrogen. Dry dimethylformamide (1.5 l) was added. Benzyl alcohol (400 ml) was then added at such a rate to keep the temperature below 50° C. The addition took 2 hours. Epichlorohydrin (92.5 g, 1 mol) was then added dropwise over 0.5 hour with ice cooling in order to keep the temperature below 40° C. The solution was next stirred for 16 hours at 21° C. then for 2.5 hours at 50° C. The dimethylformamide was then removed by evaporation at reduced pressure. The oily residue was dissolved in 2.5 l diethyl ether. The organic solution was washed with 2 l of water, 2 l of 2% hydrochloric acid, 2 l of 1% sodium bicarbonate, and 1 l of brine, dried over sodium sulfate, and concentrated to a brown oil. Distillation gave 147.8 g of 1,3-di-O-benzylglycerol (bp 170°–180° C./1 torr).

PREPARATION II

Preparation of 1,3-Di-O-benzyl-2-O-chloromethylglycerol

Dry hydrogen chloride gas was bubbled for 1.5 hours into a solution of 1,3-di-O-benzylglycerol from Preparation I (15 g, 55 mmol) and paraformaldehyde (3.3 g, 110 mmol) in 175 ml of 1,2-dichloroethane at 0° C. The solution was then stored in a stoppered flask for 21 hours at 4° C. Next, the solution was dried over magnesium sulfate with warming to 21° C. then filtered and concentrated to give 17.5 g of 1,3-di-O-benzyl-2-O-chloromethylglycerol.

PREPARATION III

Preparation of 2-O-Acetoxymethyl-1,3-di-O-benzylglycerol

To a solution of 1,3-di-O-benzyl-2-O-chloromethylglycerol from Preparation II (17.5 g, 55 mmol) in 400 ml of dimethylformamide at 0° C. under a drying tube was added sodium acetate (6 g). The solution was then warmed to 21° C. and magnetically stirred for 15 hours. The solvent was removed by evaporation at reduced pressure and the oily residue dissolved in 1 pound of diethylether. The ether solution was washed once with 750 ml of water, two times with 250 ml of water, and once with 250 ml of brine, dried over sodium sulfate and concentrated to give 19 g of 2-O-acetoxymethyl-1,3-di-O-benzylglycerol as an oil.

PREPARATION IV

Preparation of $N^2$,9-Diacetylguanine

Guanine (20 g, 0.132 mol) was combined with 300 ml of acetic anhydride and the mixture heated at reflux for 16 hours. The mixture was cooled and the excess acetic anhydride removed by evaporation at reduced pressure. The residue was recrystallized from dimethyl sulfoxide to give 25.6 g of $N^2$,9-diacetylguanine.

PREPARATION V

A. Preparation of $N^2$-Acetyl-9-(1,3-dibenzyloxy-2-propoxymethyl)guanine $N^2$,9-Diacetylguanine from Preparation IV (15.61 g, 66 mmol), 2-O-acetoxymethyl-1,3-di-O-benzylglycerol from Preparation III (19 g, 55 mmol), and bis(p-nitrophenyl)phosphate (0.5 g) were stirred together with 150 ml of diethylether. The solvent was removed by evaporation and the residue heated in a 175° C. oil bath for 1.5 hours under a stream of nitrogen. Column chromatography eluting with 1:9 methanol/methylene chloride followed by recrystallization from ethyl acetate afforded 4.76 g of $N^2$-acetyl-9-(1,3-dibenzyloxy-2-propoxymethyl)guanine, mp 145–146° C.

B. Preparation of $N^2$-Acetyl-9-(1,3-dihydroxy-2-propoxymethyl)guanine

To a solution of $N^2$-acetyl-9-(1,3-dibenzyloxy-2-propoxymethyl)guanine (4.62 g, 9.67 mmol) in 150 ml of methanol plus 40 ml of water was added 20% palladium hydroxide on carbon as a slurry in 10 ml of water. The mixture was hydrogenated on a Parr hydrogenator at 60 psi of hydrogen for 38 hours then filtered through celite and concentrated to a white solid. Recrystallization from methanol/ethyl acetate gave 1.4 g of $N^2$-acetyl-9-(1,3-dihydroxy-2-propoxymethyl)guanine, mp 205–208° C.

The mother liquor was further reduced with 10% palladium on carbon (1 g) in 150 ml of methanol plus 50 ml of water at 60 psi for 47 hours. The total yield of $N^2$-acetyl-9-(1,3-dihydroxy-2-propoxymethyl)guanine was 2.11 g.

C. Preparation of 9-(1,3-Dihydroxy-2-propoxymethyl)guanine $N^2$-Acetyl-9-(1,3-dihydroxy-2-propoxymethyl)guanine (721.9 mg, 2.4 mmol) was stirred with 50 ml of methanolic ammonia solution (methanol saturated with ammonia at 0° C.) for 17 hours at 21° C. The solution was concentrated to a white solid and the residue recrystallized from methanol to give 582.3 mg of 9-(1,3-dihydroxy-2-propoxymethyl)guanine, mp 250° C. d.

PREPARATION VI

A. 9-(1,3-Dihydroxy-2-propoxymethyl)guanine (3.0 g) imidazole (2.0 g), t-butyldimethylsilylchloride (2.13 g) and dry dimethylformamide (40 mL) were stirred together at 0° C. for 2 hours then evaporated in vacuo. The syrupy residue was taken in water causing the precipitation of crude product. The solid was filtered off, rinsed with water, then with toluene, and then dried in vacuo.

B. To a 0° C. solution of the dried, crude mono-t-butyldimethylsilyl derivative prepared in Part (A) in pyridine (100 mL) was added benzoyl chloride (5 mL). The mixture was allowed to come to room temperature (21° C.) and left for 24 hours before evaporation in vacuo. The residue was chromatographed on a column of silica gel (300 g) using gradient elution consisting of 2 L of dichloromethane and 2 L of 5% methanol in dichloromethane. A crude separation afforded 3.5 g of amber foam consisting mainly of 9-(1-benzoyloxy-3-t-butyldimethylsilyloxy-2-propoxymethyl)-$N^2$-benzoylguanine.

C. The crude product prepared in Part B was treated directly with 80% acetic acid (50 mL) at 80° C. for 3½ hours. After evaporation of the solvent, the resulting residue was chromatographed on a column of silica gel (500 g) using 8% methanol in dichloromethane as solvent. Evaporation of appropriate fractions left pure 9-(1-benzoyloxy-3-hydroxy-2-propoxymethyl)-$N^2$-benzoylguanine (611 mg) as a foam.

PREPARATION VII

A solution of 9-(1,3-dihydroxy-2-propoxymethyl)-guanine (8.18 g), monomethoxytrityl chloride (21.7 g) triethylamine (13.3 ml) and 4-dimethylaminopyridine (0.08 g) in dimethylformamide (100 ml) was stirred under anhydrous conditions for 2 hours at 40° C., quenched with methanol and then evaporated in vacuo. The crude product was dissolved in ethyl acetate (500 ml) and the solution washed with aqueous sodium bicarbonate (500 ml, 300 ml) and water (300 ml), dried over magnesium sulfate, and then evaporated in vacuo. The crude product was heated in ethanol (800 ml), cooled and filtered. The filtrate was evaporated in vacuo then chromatographed on a column of silica gel (500 g) eluting with 1:14 methanol/dichloromethane (v/v). The product was crystallized from ethanol leaving 11.2 g of 9-(1-hydroxy-3-monomethoxytrityl-2-propoxymethyl)-guanine-$N^2$-monomethoxytritylguanine, m.p. 159°–160° C.

EXAMPLE 1

To a stirred suspension of 9-(1-benzoyloxy-3-hydroxy-2-propoxymethyl)-$N^2$-benzoylguanine (463 mg) prepared in Preparation VI in ethyl acetate (10 mL) cooled to 0° C., was added pyrophosphoryl chloride (0.75 ml). After 2 hours, the reaction was quenched by the addition of ice, then brought to pH 5 by the addition of solid sodium hydrogen carbonate, causing the phosphorylated product to oil out of solution. The supernatant was decanted off and the remaining residue was dissolved in water and extracted with 10% butanol in dichloromethane (v/v). The aqueous phase was evaporated in vacuo leaving nearly pure, fully protected phosphorylated product. This product was treated directly with concentrated ammonium hydroxide (10 ml) for 16 hours at 40° C. The solution was then evaporated in vacuo to a wet solid which was dissolved in water and extracted with 10% butanol in dichloromethane (v/v). The aqueous phase was then applied onto a column of Sephadex G-10 resin (1"×30") and eluted with water. Pure product-containing fractions were pooled, concentrated by evaporation, then lyopholyzed to give the 1-(monophosphate ester) of 9-(1,3-dihydroxy-2-propoxymethyl)guanine sodium ammonium salt (276 mg) m.p. 215°–220° C. as an amorphous solid.

EXAMPLE 2

To a 0° C. stirred suspension of 9-(1,3-dihydroxy-2-propoxymethyl)guanine (500 mg) in ethyl acetate (20 ml) was added pyrophosphoryl chloride (1.5 ml) dropwise over 3 minutes. After 2 hours, the now clear reaction mixture was quenched by the addition of ice (10 g), then neutralized with solid sodium hydrogen carbonate. The aqueous phase was isolated and purified on a column of Sephadex G-10 resin, using water as eluent. Evaporation of appropriate fractions gave a sirupy residue which crystallized from dimethylformamide. Rinsing the crystals with methanol and drying in vacuo gave 725 mg of pure 1,3-bis(monophosphate ester) of 9-(1,3-dihydroxy-2-propoxymethyl)guanine as the tetrasodium salt.

EXAMPLE 3

The 1-monophosphate ester of 9-(1,3-dihydroxy-2-propoxymethyl)guanine disodium salt (180 mg) was converted to the free acid by passage through a column of Dowex 50-X8 cation exchange resin (10 mL) using water as eluent. Evaporation of the water left the free acid as a colorless glass (170 mg). This residue was dissolved in a mixture of pyridine (10 mL) and water (5 mL) containing 4-morpholino-N,N'-dicyclohexylcarboxamidine (138 mg) and then evaporated in vacuo. The residue was then co-evaporated three times with 10 mL portions of pyridine. A solution of the resulting foam in pyridine (60 mL) was added dropwise over 45 minutes to a refluxing solution of dicyclohexylcarbodiimide (194 mg) in pyridine (50 mL). When addition was complete, tne mixture was refluxed for an additional 2.75 hours before being evaporated in vacuo to a white solid. A solution of the solid in water (30 mL) was extracted three times with an equal volume of ether, then concentrated in vacuo to approximately 1 mL. The concentrated solution was purified by preparative high pressure liquid chromatography using multiple injections onto a column (1 cm×25 cm) of Partisil SAX-10 resin. The column was eluted with a buffer gradient consisting of 0.02M to 0.08M potassium dihydrogen phosphate (pH 6.8) over 20 minutes. Eluents containing pure cyclic phosphate of compound of formula (I) were combined and evaporated to a solid (535 mg) which was desalted by passage down a column (5 cm×60 cm) of Sephadex G-10 resin using water as eluent. The pure desalted product was collected and lyopholyzed from water, leaving the cyclic phosphate ester of 9-(1,3-dihydroxy-2-propoxymethyl)guanine as the monopotassium salt. (82 mg), m.p. dec. ~250° C.

EXAMPLE 4

A mixture of $N^2$-monomethoxytrityl-9-(1-monomethoxytrityloxy-3-hydroxy-2-propoxymethyl)guanine (1.70 g) and dicyclohexylcarbodiimide (2.68) in 0.13 M cyanoethylphosphate in pyridine (50 ml) was stirred at 21° C. for 2.5 days before quenching by the addition of water (10 ml). The solution was evaporated in vacuo and the residue treated with concentrated ammonium hydroxide (80 ml) for 2 hours at 60° C., then re-evaporated in vacuo. The residue was dissolved in 80% (v/v) acetic acid and heated at 80° C. for 2 hours, then left at 21° C. for 16 hours before evaporation in vacuo. The residue was taken in water (80 ml) and the solution extracted with dichloromethane (3×50 ml). The aqueous phase was filtered, concentrated to approximately 10 ml, basified with concentrated ammonium hydroxide and applied onto a column (5.5 cm×40 cm) of Sephadex G-10 gel. Elution with water and evaporation of the fractions containing pure product left 520 mg of amorphous 9-(1-monophosphate-3-hydroxy-2-propoxymethyl)guanine as the diammonium salt.

EXAMPLE 5

A compound of formula (I), prepared in accordance with Examples 1, 2 or 3 is dissolved in ethanol and an excess of calcium chloride in ethanol is added to the mixture at room temperature and stirred. The resulting calcium salt precipitates out. The calcium salt is then transformed into other corresponding salts by passing the salt as a solution through DOWEX 50 resin with the corresponding counter ion desired on the resin.

Similarly, using the above procedure one obtains, for example, the following compounds:

1-(monophosphate ester) of 9-(1,3-dihydroxy-2-propoxymethyl)guanine diammonium salt;

1-(monophosphate ester) of 9-(1,3-dihydroxy2-propoxymethyl)guanine bis(trimethylammonium) salt;

1-(monophosphate ester) of 9-(1,3-dihydroxy2-propoxymethyl)guanine bis(diethylammonium) salt;

1-(monophosphate ester) of 9-(1,3-dihydroxy2-propoxymethyl)guanine di(cyclohexylammonium) salt;

1-(monophosphate ester) of 9-(1,3-dihydroxy2-propoxymethyl)guanine dimorpholinium salt;

1-(diphosphate ester) of 9-(1,3-dihydroxy2-propoxymethyl)guanine triammonium salt;

1-(triphosphate ester) of 9-(1,3-dihydroxy2-propoxymethyl)guanine tetrakis(trimethylammonium) salt;

1,3-bis(monophosphate ester) of 9-(1,3-dihydroxy2-propoxymethyl)guanine tetrakis(triethylammonium) salt.

cyclic phosphate ester of 9-(1,3-dihydroxy2-propoxymethyl)guanine ammonium salt;

cyclic phosphate ester of 9-(1,3-dihydroxy2-propoxymethyl)guanine trimetnylammonium salt;

cyclic phosphate ester of 9-(1,3-dihydroxy2-propoxymethyl)guanine diethylammonium salt;

cyclic phosphate ester of 9-(1,3-dihydroxy2-propoxymethyl)guanine dicyclonexylammonium salt; and cyclic phosphate ester of 9-(1,3-dinydroxy2-propoxymethyl)guanine morpholinium salt.

EXAMPLE 6

The following example illustrates the preparation of representative pnarmaceutical formulations containing an active compound of Formula (I).

| A. Topical Formulation | |
|---|---|
| Active compound | 0.2–2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water gs | 100 ml |

All of the above ingredients, except water, are combined and heated at 60° C. with stirring. A sufficient quantity of water at 60° C. is then added with vigorous stirring to provide 100 g of the cream formulation which is then cooled to room temperature.

The following formulation is useful for intraperitoneal and intramuscular injection.

| B. IP and IM Formulation | |
|---|---|
| Active compound | 0.5 g |
| Propylene glycol | 20 g |
| Polyethylene glycol | 20 g |
| Tween 80 | 1 g |
| 0.9% Saline solution gs | 100 ml |

The active compound is dissolved in propylene glycol, polyethylene glycol 400 and Tween 80. A sufficient quantity of 0.9% saline solution is then added with stirring to provide 100 ml of the I.P. or I.M. solution which is filtered through a 0.2 micron membrane filter and packaged under sterile conditions.

The following formulation is useful for intravenous injection.

| C. I.V. Formulation | |
|---|---|
| Active compound | 0.5 g |
| 0.9% Saline solution | 100 g |

The active compound is added to 100 ml of 0.9% saline solution with stirring to provide 100 ml of I.V. solution which is filtered through a 0.2 micron membrane filter and packaged under sterile conditions.

| D. Tablet Formulation | |
|---|---|
| | Parts by weight |
| Active compound | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg of active compound) with an appropriate tabletting machine.

What is claimed is:

1. A process for preparing a compound of the formula

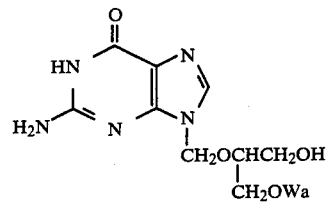

(I)

wherein Wa is

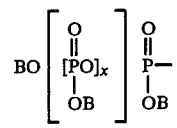

wherein each B is independently hydrogen or a pharmaceutically acceptable counterion, which process comprises contacting a solution of a compound of the formula

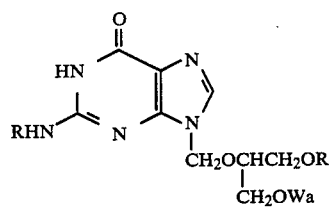

(XIV)

wherein R is benzoyl or a triphenylmethyl group and Wa is as defined above with an acid or a base for a time sufficient to form compound of formula (I).

2. The process of claim 1 wherein R is benzoyl.
3. The process of claim 1 wherein R is a triphenylmethyl group.
4. The process of claim 2 wherein the solution of the compound of formula (XIV) is contacted with a base.
5. The process of claim 3 wherein the solution of the compound of formula (XIV) is contacted with an acid.
6. A process for preparing a compound of the formula

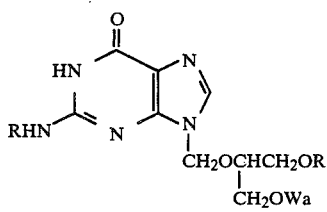
(XIV)

wherein Wa is

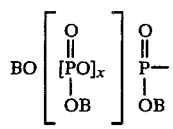

wherein each B is independently hydrogen or a pharmaceutically acceptable counterion and R is benzoyl which comprises (a) contacting a solution of a compound of the formula

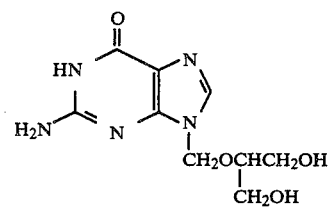
(X)

with t-butyldimethylsilyl chloride at −5° C. to room temperature for ½ to 4 hours to form a silyl-protected compound of the formula

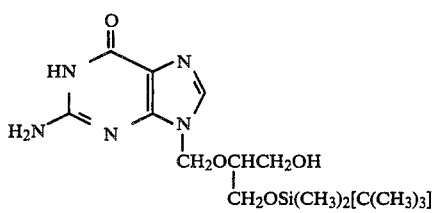
(XI)

(b) contacting a solution of the compound formed in (a) with benzoyl chloride at −5° C. to 10° C. for 18 to 36 hours to form a compound of the formula

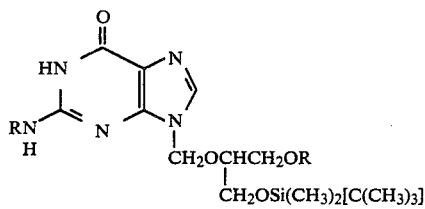
(XII)

wherein R is benzoyl;

(c) removing the silyl protecting group from the compound formed in (b) by treating compound of formula (XII) with an acid at 50° C. to 100° C. for 1 to 6 hours to form a compound of the formula

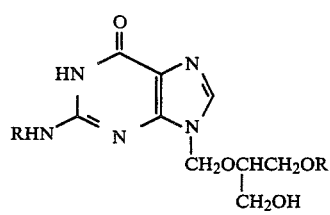
(XIII)

wherein R is benzoyl; and (d) contacting a solution of the compound formed in (c) with a phosphorylating agent at −5° C. to 10° C. for 1 to 4 hours to form a compound of formula (XIV).

7. The process of claim 6 wherein the phosphorylating agent in (d) is pyrophosphoryl chloride.

8. A process for preparing a compound of the formula

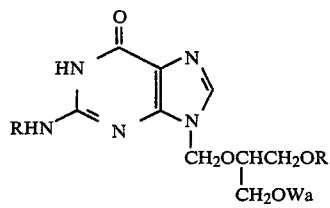
(XIV)

wherein Wa is

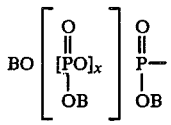

wherein each B is independently hydrogen or a pharmaceutically acceptable counterion, and R is a triphenylmethyl group which comprises (a) contacting a solution of a compound of the formula

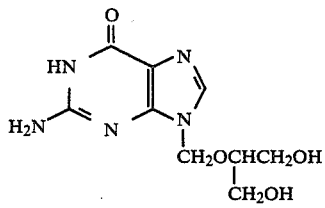
(X)

with a triphenylmethyl chloride at 25° C. to 60° C. for ½ to 4 hours to form a compound of the formula

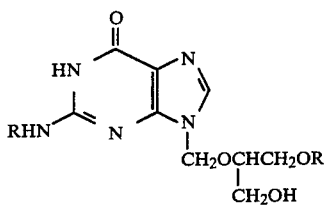

(XIII)

wherein R is a triphenylmethyl group; and (b) contacting a solution of the compound formed in (a) with a phosphorylating agent at 15° C. to 30° C. for 1 to 5 days to form a compound of formula (XIV).

9. The process of claim 8 wherein the triphenylmethyl chloride is triphenylmethyl chloride or 4-methoxyphenyl(diphenyl)methyl chloride.

10. The process of claim 8 wherein the phosphorylating agent is cyanoethylphosphate.

11. A process for preparing a compound of the formula

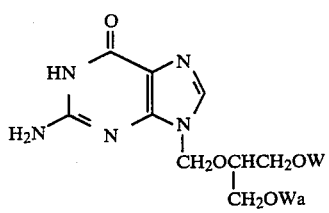

(I)

wherein W and Wa are each

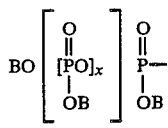

wherein each B is independently hydrogen or a pharmaceutically acceptable counterion, which process comprises contacting a solution of a compound of the formula

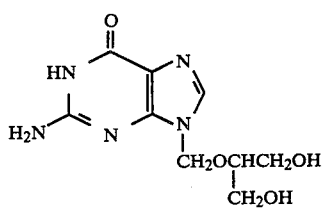

(X)

with a phosphorylating agent at −5° C. to 10° C. for 1 to 4 hours

12. The process of claim 11 wherein the phosphorylating agent is pyrophosphoryl chloride.

13. A process for preparing a compound of the formula

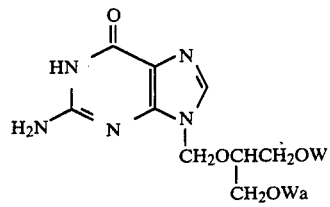

(I)

wherein W together with Wa is

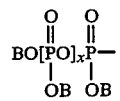

wherein B is hydrogen or a pharmaceutically acceptable counterion which process comprises cyclizing a compound of the formula

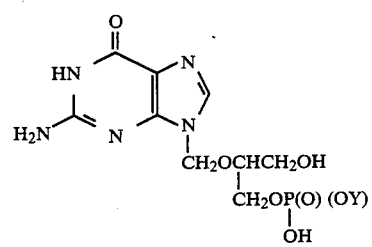

(XV)

by heating a solution of compound of formula (XV) in the presence of a condensing agent wherein Y is a lipophilic amine for ½ to 4 hours.

14. The process of claim 13 wherein the condensing agent is dicyclohexylcarbodiimide.

15. The process of claim 14 wherein the lipophilic amine is 4-morpholino-N,N'-dicyclohexylcarboxamidine.

16. A process for preparing a compound of the formula

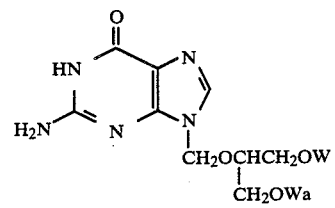

(I)

wherein W and Wa are each

BO[PO]$_x$P— wherein each B is independently hydrogen or a pharmaceutically acceptable counterion and x is 1 or 2 which process comprises contacting a solution of a compound of the formula

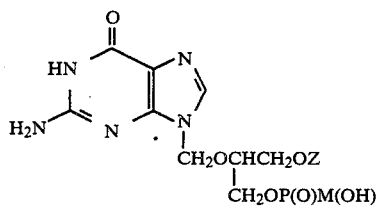
(XVI)
wherein Z is hydrogen or P(O)M(OH) and M is 4-morpholino with tributylammonium phosphate or tributylammonium pyrophosphate at 40° C. to 50° C. for 6 to 16 hours.
17. The process of claim 16 wherein x is 1 and the phosphorphating agent in tributylammonium phosphate.
18. The process of claim 16 wherein x is 2 and the phosphorphating agent in tributylammonium pyrophosphate.
* * * * *